United States Patent
Liu et al.

(10) Patent No.: US 11,812,934 B2
(45) Date of Patent: Nov. 14, 2023

(54) CAPSULE ENDOSCOPE SYSTEM, METHOD OF IDENTIFYING STAINED AREA IN ENDOSCOPIC IMAGES AND COMPUTER READABLE STORAGE MEDIUM

(71) Applicants: ANKON TECHNOLOGIES CO., LTD, Wuhan (CN); ANX IP HOLDING PTE. LTD., Singapore (SG)

(72) Inventors: Hui Liu, Wuhan (CN); Wenjin Yuan, Wuhan (CN); Hang Zhang, Wuhan (CN); Zhiwei Huang, Wuhan (CN); Hao Zhang, Wuhan (CN)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 131 days.

(21) Appl. No.: 17/150,969

(22) Filed: Jan. 15, 2021

(65) Prior Publication Data
US 2021/0219829 A1    Jul. 22, 2021

(30) Foreign Application Priority Data
Jan. 16, 2020  (CN) .......................... 202010047174.9

(51) Int. Cl.
*A61B 1/04* (2006.01)
*A61B 1/273* (2006.01)
*A61B 1/00* (2006.01)

(52) U.S. Cl.
CPC ........ *A61B 1/041* (2013.01); *A61B 1/000094* (2022.02); *A61B 1/273* (2013.01)

(58) Field of Classification Search
CPC .......... A61B 1/00009; A61B 1/000094; A61B 1/041; G06T 2207/10068;
(Continued)

(56) References Cited

U.S. PATENT DOCUMENTS

2013/0121546 A1* 5/2013 Guissin ................. G06T 7/0012
                                                          382/128
2015/0193929 A1* 7/2015 Ikemoto ........... A61B 1/000095
                                                          382/128
(Continued)

FOREIGN PATENT DOCUMENTS

CN          105869155 A   *   8/2016

OTHER PUBLICATIONS

Charisis et al. "Capsule endoscopy image analysis using texture information from various colour models". Jul. 2012. Computer Methods and Programs in Biomedicine, vol. 107, Issue 1, pp. 61-74. (Year: 2012).*

(Continued)

*Primary Examiner* — Aaron B Fairchild
*Assistant Examiner* — Julianna J Nicolaus
(74) *Attorney, Agent, or Firm* — Treasure IP Group, LLC

(57) ABSTRACT

The present invention discloses a capsule endoscope system, a method of identifying stained area in endoscopic images, and a computer readable storage medium. The method comprises: obtaining a basic image taken by a photographing device; removing abnormal pixels from the basic image and recording it as a processed image; obtaining the hue, saturation and value of each pixel in the processed image of HSV format; setting a first condition that the hue is in a D1 range, the saturation is in a D2 range, and the value is in a D3 range; obtaining the b component of each pixel in the processed image of Lab format; setting a second condition that the b component is in a D4 range; collecting and processing the pixels that meet the first condition and/or the second condition to form a set C; calculating the initial range area S1 of the set C.

13 Claims, 2 Drawing Sheets

(58) Field of Classification Search
CPC . G06T 2207/30028; G06T 2207/30092; G06T 7/0012
See application file for complete search history.

(56) References Cited

U.S. PATENT DOCUMENTS

2019/0021580 A1* 1/2019 Mishima .......... A61B 1/000095
2021/0398321 A1* 12/2021 Wilander ............. G06V 20/698

OTHER PUBLICATIONS

"Capsule endoscopy image analysis using texture information from various colour models." Vasileios S. Charisisa, Leontios J. Hadjileontiadisa,?, Christos N. Liatsosb,c, Christos C. Mavrogiannisc, George D. Sergiadisa. Computer methods and programs in biomedicine. 107 (2012) 61-74.

* cited by examiner

CAPSULE ENDOSCOPE SYSTEM, METHOD OF IDENTIFYING STAINED AREA IN ENDOSCOPIC IMAGES AND COMPUTER READABLE STORAGE MEDIUM

CROSS-REFERENCE OF RELATED APPLICATIONS

The application claims priority to Chinese Patent Application No. 202010047174.9 filed on Jan. 16, 2019, the contents of which are incorporated by reference herein.

FIELD OF INVENTION

The present invention relates to a capsule endoscopy technique, and more particularly to a capsule endoscope system, a method of identifying stained area in endoscopic images, and a computer readable storage medium.

BACKGROUND

In the treatment of gastrointestinal diseases, medications such as mucosal protective agents are used more often. Such type of medication has the effect of protecting and enhancing the defense function of gastrointestinal mucosa. After entering gastrointestinal tract, the medication covers the mucosa and protects the mucosa from being attacked by various harmful substances, thereby enhancing the defense and repair effect of the mucosa, and improving the healing ability of the mucosa.

In order to evaluate the effectiveness of mucosal protective agent, some harmless stains are used to stain the gastrointestinal mucosa, resulting in enhanced contrast between the lesion site and the surrounding mucosa, and clearer mucosal structure and contours, which can improve the evaluation on the mucosal protective agent.

As a swallowable device, capsule endoscope has been widely used in gastrointestinal examinations. The capsule endoscope is powered by an internal battery and relies on a camera module to take images of the gastrointestinal tract, which are transmitted wirelessly outside the body. However, there is no method available to recognize the stained area in the images taken by the capsule endoscope, so it is not possible to visually evaluate the healing of the mucosa and the effect of mucosal protective agents in conjunction with the capsule endoscope.

Therefore, it is necessary to design a capsule endoscope system, a method of identifying stained area in endoscopic images, and a computer readable storage medium.

SUMMARY OF THE INVENTION

The present invention discloses a method of identifying stained area in endoscopic images, comprising:
obtaining a basic image taken by a photographing device;
removing abnormal pixels from the basic image and recording it as a processed image;
obtaining the hue, saturation and value of each pixel in the processed image of HSV format;
setting a first condition that the hue of the pixel is in a D1 range, the saturation is in a D2 range, and the value is in a D3 range;
obtaining the b component of each pixel in the processed image of Lab format;
setting a second condition that the b component of the pixel is in a D4 range;
collecting and processing the pixels that meet the first condition and/or the second condition to form a set C;
calculating the initial range area S1 of the set C.

In an embodiment, the step "removing abnormal pixels from the basic image and recording it as a processed image" comprises:
converting the basic image to a grayscale format;
obtaining a set of pixels with grayscale values in a Grange from the basic image and recording it as a processed image.

In an embodiment, the Grange is [10,240].

In an embodiment, in the step "setting a first condition that the hue of the pixel is in a D1 range, the saturation is in a D2 range, and the value is in a D3 range", the D1 range is [0.43,0.7], the D2 range is [0.16,1], the D3 range is [0.16,1], and the hue, the saturation, and the value are normalized.

In an embodiment, the D4 range is $$\left[\frac{1}{4}B_{min}, 0.16\right],$$

and the b component is normalized, and wherein $B_{min}$ is the minimum value of the b component of the basic image in a Lab color model.

In an embodiment, after the step "calculating the initial range area S1 of the set C" further comprises:
determining the staining of the basic image;
when the staining of the stained region is completely stained, calculating the ratio of the initial range area S1 of the set C to the total area of the basic image, and obtaining the ratio of the stained area;
when the staining of the stained region is poor, calculating the deep stained area S2, calculating the ratio of the deep stained area S2 to the total area of the basic image, and obtaining the ratio of the stained area.

In an embodiment, the step "determining the staining of the basic image" comprises:
taking 0 as the value of the pixels in the processed image with hue is in a range H1, taking 1 as the value of the pixels in the processed image with hue in a range H2, and the minimum value in the range H2 is greater than the maximum value in the range H1;
calculating the area Sh of the pixels whose value is taken as 1;
obtaining a threshold T1;
when Sh>T1, determining that the staining of the stained region in the basic image is poor;
when Sh<T1, determining that the staining of the stained region in the basic image is completely stained.

In an embodiment, the range H1 is [0, T the range H2 is $(T_2,1]$, the value range of T2 is [0.01,0.2], the value range of T1 is [0.6,0.98], and the hue is normalized.

In an embodiment, the step "calculating the deep stained area S2" comprises:
calculating the RGB value of each pixel in the processed image, x(i,j)=(r,g,b);
calculating the HSV value of each pixel in the processed image, $x_2(i,j)$=(h,s,v);
calculating the blue change value $f_b(i,j)$ of each pixel, $$f_b(i, j) = \alpha * \frac{b}{r} + \beta * \frac{b}{g} + \gamma * \frac{b}{h};$$

obtaining a blue change value threshold $T_3$;

obtaining the set of all pixels, of which $f_b(i,j) > T_3$, and calculating the deep stained area S2.

In an embodiment, the value range of $\alpha$, $\beta$, $\gamma$ is [0,3].

In an embodiment, the step "obtaining the blue change value threshold $T_3$" comprises:

calculating the blue change value threshold $T_3(i,j)$ of each pixel, $$T_3(i,j) = \alpha * th1 + \beta * th2 + \gamma * th3;$$

th1 is the threshold of $$\frac{b}{r},$$

th2 is the threshold of $$\frac{b}{g},$$

th3 is the threshold of $$\frac{b}{h};$$

the step "obtaining the set of all pixels, of which $f_b(i,j) > T_3$, and calculating the deep stained area S2" comprises:

calculating the magnitude of $f_b(i,j)$ and $T_3(i,j)$ of each pixel, respectively;

obtaining the set of all pixels, of which $f_b(i,j) > T_3(i,j)$, and calculating the deep stained area S2.

In an embodiment, the relationship between th1 and r of the pixel is obtained by the following formula:

$$th1 = \varepsilon * r + \varepsilon_2;$$

the value range of $\varepsilon_1$ is [−1,1], the value range of $\varepsilon_2$ is [−2,5].

In an embodiment, the value range of th2 is [0.7,2.2], the value range of th3 is [1,2].

The present invention further provides a capsule endoscope system. The capsule endoscope system comprises a capsule endoscope and an external device. The external device comprises a memory and a processor. The memory stores computer programs that run on the processor, and the processor executes the computer programs to implement the steps in the method of identifying the stained area in images as described above.

The present invention further provides a computer readable storage medium for storing computer programs. The computer programs are executed by the processor to implement the steps in the method of identifying the stained area in images described above.

In the present invention, since the color difference between a lesion site and the normal site on the gastrointestinal mucosa is large after the gastrointestinal tract is stained, it can selectively identify the hue, saturation and value of each pixel and b component of each pixel in the basic image to determine the stained site, and thus to further analyze the recovery of gastrointestinal mucosa and the efficacy of mucosal protective agent. Moreover, in the present invention, abnormal pixels are removed from the basic image to further improve the accuracy of pixel determination.

DETAILED DESCRIPTION

In order to enable those skilled in the art to better understand the technical solutions disclosed, the present invention can be described in detail below with reference to the accompanying drawings and preferred embodiments. However, the embodiments are not intended to limit the invention, and obviously, the described embodiments are only a part of the embodiments of the present invention, but not all of them. All other embodiments obtained by those having ordinary skill in the art without creative work based on the embodiments of the present invention are included in the scope of the present invention.

Figure 1:
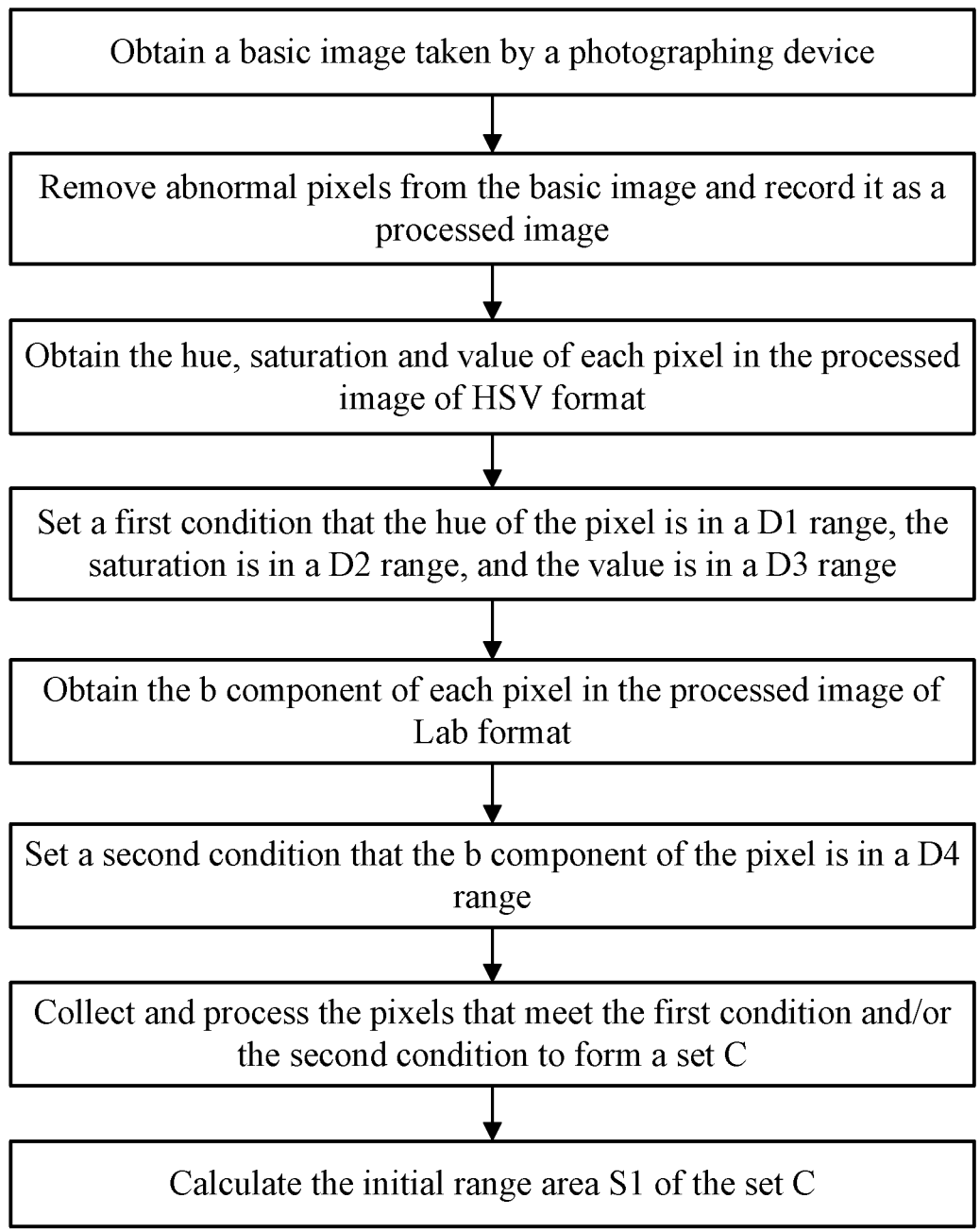
FIG. 1 a schematic flowchart of a method of identifying stained area in endoscopic images according to aspects of the present invention.
Figure 2:
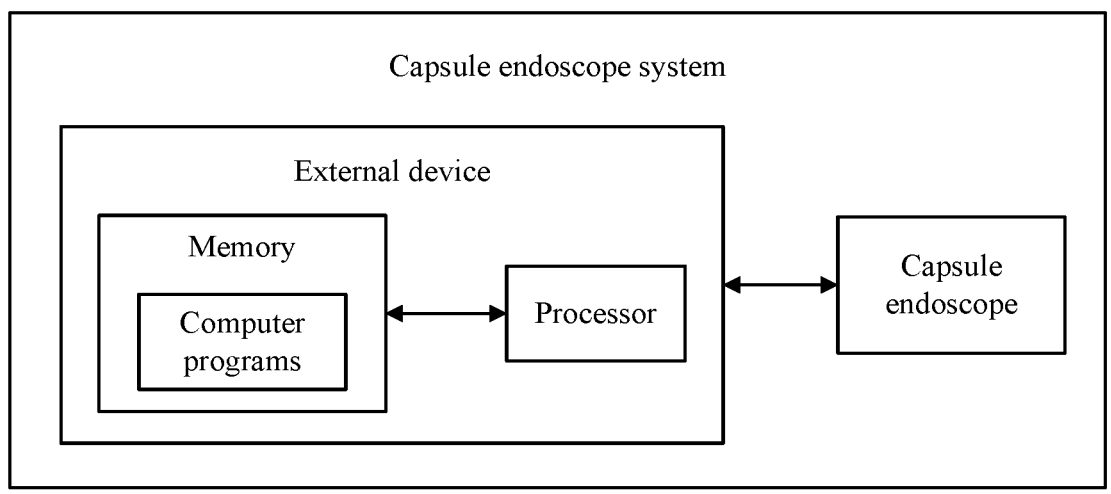
FIG. 2 is a schematic illustration of a capsule endoscope system according to the aspect of the present invention.

Referring to FIG. 1, the present invention discloses an method of identifying stained area in endoscopic images, comprising:

obtaining a basic image taken by a photographing device;

removing abnormal pixels from the basic image and recording it as a processed image;

obtaining the hue, saturation and value of each pixel in the processed image of HSV format;

setting a first condition that the hue of the pixel is in a D1 range, the saturation is in a D2 range, and the value is in a D3 range;

obtaining the b component of each pixel in the processed image of Lab format;

setting a second condition that the b component of the pixel is in a D4 range;

collecting and processing the pixels that meet the first condition and/or the second condition to form a set C;

calculating the initial range area S1 of the set C.

Since the color difference between a lesion site and the normal site on the gastrointestinal mucosa is large after the gastrointestinal tract is stained, it is possible to selectively identify the hue, saturation and value of each pixel and b component of each pixel in the basic image to determine the stained site, and thus to further analyze the recovery of gastrointestinal mucosa and the efficacy of mucosal protective agent. Moreover, in the present invention, abnormal pixels are removed from the basic image to further improve the accuracy of pixel determination.

In addition, the photographing device is a capsule endoscope.

In the present invention, usually, the stain is blue. After the gastrointestinal mucosa is stained using a blue stain, the stained site presents blue that is visible in the images taken by the capsule endoscope. The unstained site presents red, so the contrast is more significant.

The step "removing abnormal pixels from the basic image and recording it as a processed image" comprises:

converting the basic image to a grayscale format;

obtaining a set of pixels with grayscale values in a G range from the basic image and recording it as a processed image.

Due to the uneven exposure of the capsule endoscope, the basic image is prone to overexposure or underexposure, and the overexposed and underexposed pixels are abnormal pixels, which, if not removed, can affect the accuracy of subsequent calculations.

Therefore, in the present invention, when the basic image is converted to grayscale format, the grayscale value of underexposed pixels is smaller while the grayscale value of overexposed pixels is larger. Moreover, in the specific embodiment, a mask MASK1 with a grayscale value in the G range can be made to cover the basic image to remove overexposed or underexposed pixels.

The range of grayscale value is [0,255]. In the specific embodiment, the G range is [10,240]. Then, the pixels whose grayscale values are not within the G range are abnormal pixels and cannot be involved in the subsequent analysis. The G range can be adjusted according to the specific exposure of the basic image. Preferably, the G range can be set to [35,240].

Further, in the step "setting a first condition that the hue of the pixel is in a D1 range, the saturation is in a D2 range, and the value is in a D3 range", the D1 range is [0.43,0.7], the D2 range is [0.16,1], the D3 range is [0.16,1], and the hue, saturation, and value are normalized. It should be noted that since the stain used in the present invention is blue, the values of hue, saturation, value, and b component are within a certain range. If stains of other colors are used, the values of hue, saturation, value, and b component are in other range, which can also achieve the object of the present invention.

Before obtaining the hue, saturation and value of each pixel in the processed image, the basic image must be converted to HSV format. HSV is a color model, including hue, saturation, and value. Typically, hue is measured in angles, and the value range is 0°~360°, where red is 0°, green is 120°, and blue is 240°. The value range of saturation and value is usually 0 to 255. In the specific embodiment, the hue, saturation, and value are normalized for ease of calculation. For ease of understanding, in fact, 0.43*360≈154, 0.7*360=252, D1 range is [154,252], which covers the range of green and blue colors in the basic image, and thus the object of the present invention can be achieved. The saturation and value are calculated in the same way, and the range is further divided by saturation and value to make the result more accurate, which is not repeated here.

Of course, similar to the removal of abnormal pixels, in the step, a mask MASK2 meeting the first condition can also be made and covered with the mask MASK1 on the basic image.

As described above, the color of the stain is blue, so the blue area is divided by the D1, D2 and D3 ranges.

Since the D1, D2, and D3 ranges can also be adjusted according to the specific image, preferably, the D1 range can beset to [0.51,0.68], the D2 range can beset to [0.188,1], and the D3 range can be set to [0.188,1].

And, due to the difference in staining of different tissues, a blue stain may not necessarily stain the mucosa into standard blue during staining, but instead achieve a complete staining presented in diverse colors such as blue, dark blue, light blue, dark green, etc. The basic image may present green. Therefore, in the present invention, it is possible to either use a single first condition using HSV format or a second condition using Lab format, or use the first condition and second condition together to determine the set C.

Lab color model is a digital way to describe human visual perception and mainly reflects human perception of color changes. Where L represents lightness, a component represents a change from green to red, b component represents a change from blue to yellow, and the change from blue to yellow also covers green. And, the value range of L is [0,100], and the value range of a and b are both [0,255].

In the specific embodiment, the Lab color model is further analyzed to form the set C, and the initial range area S1 can be more accurate. Also, it is possible to choose whether it is necessary to add the image processing steps of Lab color model according to different basic images. If it is necessary to add the image processing steps of Lab color model, it also can make a mask MASK3 that satisfies the second condition and cover it on the basic image together with MASK1, or the mask MASK3 can be covered on the basic image together with the mask MASK1 and MASK2.

Therefore, in the specific embodiments of the present invention, the mask MASK2 or MASK3 can be made separately for using with MASK1, or MASK2 and MASK3 can be made simultaneously for using with MASK1.

Further, since the stain in the present invention is blue, when analyzing the Lab color model, only the b component thereof can be analyzed. Specifically, the D4 range is $$\left[\frac{1}{4}B_{min}, 0.16\right],$$

and the b component is normalized, where $B_{min}$ is the minimum value of the b component of the basic image in the Lab color model. As described above, the b component is a change from blue to yellow, but the range in the image that can reflects blue not only starts with $B_{min}$, therefore, the starting point of the D4 range can be taken as $$\frac{1}{4}B_{min}.$$

Since the b component is also normalized, 0.16*255≈40, the D4 range is actually $$\left[\frac{1}{4}B_{min}, 40\right].$$

Therefore, analysis by the b component in the Lab color model while forming the mask MASK3 can make the initial range area S1 more accurate. Preferably, the D4 range can be $$\left[\frac{1}{4}B_{min}, 0.08\right].$$

Further, after the initial range area S1 is obtained, the initial range area S1 can only represent the size of a range stained blue or other derived colors in the image. However, if the staining color is inconsistent, it is determined that the initial range area S1 is not accurate enough so that the stained region needs to be further segmented.

Therefore, after the step "calculating the initial range area S1 of the set C" further comprises:
  determining the staining of the basic image;
  if the staining of the stained region is completely stained, calculating the ratio of the initial range area S1 of the set C to the total area of the basic image, and obtaining the ratio of the stained area;
  if the staining of the stained region is poor, calculating the deep stained area S2, calculating the ratio of the deep stained area S2 to the total area of the basic image, and obtaining the ratio of the stained area.

If the stained region is completely stained, the initial range area S1 can be used to calculate the percentage of the stained area to evaluate the healing of mucosa and the effectiveness of mucosal protective agent. If the stained region is poorly stained, deep stained area S2 and the percentage of stained area need to be further calculated.

The step "determining the staining of the basic image" comprises:
- taking 0 as the value of the pixels in the processed image with hue is in the range H1, taking 1 as the value of the pixels in the processed image with hue in the range H2, and the minimum value in the range H2 is greater than the maximum value in the range H1;
- calculating the area Sh of the pixels whose value is taken as 1;
- obtaining a threshold T1;
- if Sh>T1, determining that the staining of the stained region in the basic image is poor;
- if Sh<T1, determining that the staining of the stained region in the basic image is completely stained.

Thus, in this step, the basic image is also converted to HSV format, and in the HSV color model, the values of hue are binarized, and H2 and H1 do not overlap. Through comparison of the hues, and then binarizing the hues, the range of inconspicuously and incompletely stained region can be obtained. If the range is larger than T1, it means that the range of inconspicuously and incompletely stained region is large and staining effect is poor. When Sh<T1, and further Sh<T1, it indicates that the range of inconspicuously and incompletely stained region is small, and it can be determined as completely stained.

Further, the range H1 is [0, $T_2$) the range H2 is ($T_2$,1], the value range of T2 is [0.01,0.2], the value range of T1 is [0.6,0.98], where the hue is normalized.

In the embodiment, the threshold T2 used for binarization has a value of 0.08, and the value of T1 is 0.95.

If the stained region is inconspicuously or incompletely stained, the basic image can show a hazy green or blue in its entirety. So, at this point, if only hue or saturation is used for stained image division, it is very error-prone, and the entire image is easily recognized as a stained region. Therefore, the basic image is further analyzed in the present invention.

Specifically, the step "calculating the deep stained area S2" comprises:
- calculating the RGB value of each pixel in the processed image, $x_1(i,j)=(r,g,b)$;
- calculating the HSV value of each pixel in the processed image, $x_2(i,j)=(h,s,v)$;
- calculating the blue change value $f_b(i,j)$ of each pixel, $$f_b(i,j) = \alpha * \frac{b}{r} + \beta * \frac{b}{g} + \gamma * \frac{b}{h};$$

- obtaining a blue change value threshold $T_3$;
- obtaining the set of all pixels, of which $f_b(i,j)>T_3$, and calculating the deep stained area S2.

To calculate the RGB value, it is needed to first convert the processed image to RGB format, which is another color model. Where, r is red, g is green, and b is blue. A tertiary color can be produced by mixing the three colors with different components.

In the specific step, the stained region in the basic image can be determined by calculating the blue change value of each pixel. Even if the stained region is inconspicuously or incompletely stained, resulting in hazy image, the range of the stained region can still be determined to form a deep stained area S2.

Specifically, $$\frac{b}{r}$$

represents the ratio of blue value to red value of the pixel corresponding to the RGB color model;

$$\frac{b}{g}$$

H represents the ratio of blue value to green value of the pixel corresponding to the RGB color model;

$$\frac{b}{h}$$

represents the ratio of blue value of the pixel corresponding to the RGB color model to the hue corresponding to the HSV color model.

Thus, the blue color in the RGB color model can be analyzed from multiple perspectives.

In addition, wherein, α, β, γ are used as coefficients to adjust the weight of $$\frac{b}{r},$$

$$\frac{b}{g},$$

$$\frac{b}{h}$$

in the blue change value $f_b(i,j)$, thus, the value range of α, β, γ is [0,3]. Preferably, α=1, β=0, γ=0. Also, the value range of α, β, γ can be further modified according to actual conditions.

In the embodiment, the blue change value threshold $T_3$ is also different for each pixel and can change with different pixels. The object of the invention can also be achieved by comparing a blue change value threshold $T_3$ for all pixels, if any, with the blue change value $f_b(i,j)$.

The step "obtaining the blue change value threshold $T_3$" comprises:
- calculating the blue change value threshold $T_3(i,j)$ of each pixel, $$T_3(i,j)=\alpha*th1+\beta*th2+\gamma*th3;$$

th1 is the threshold of $$\frac{b}{r},$$

th2 is the threshold of $$\frac{b}{g},$$

th3 is the threshold of $$\frac{b}{h};$$

the step "obtaining the set of all pixels, of which $f_b(i,j) > T_3$, and calculating the deep stained area S2" comprises:
calculating the magnitude of $f_b(i,j)$ and $T_3(i,j)$ of each pixel, respectively;
obtaining the set of all pixels, of which $f_b(i,j) > T_3(i,j)$, and calculating the deep stained area S2.

Therefore, the blue change value threshold $T_3(i,j)$ of each pixel is calculated, and where α, β, γ, used as coefficients, are consistent with those in the calculation of the blue change value $f_b(i,j)$. Where, the value range of th2 is [0.7,2.2], the value range of th3 is [1,2]. Preferably, th2=1.3, th3=1.6.

In addition, the reason for calculating the blue change threshold $T_3(i,j)$ of each pixel is that the color of the misidentified region is found, where there is a functional relationship between $$\frac{b}{r}$$

and r at different positions, and by fitting multiple sets of data, the relationship between $$\frac{b}{r}$$

and r of the pixels in the incompletely stained region is obtained, meeting the following formula:

$$\frac{b}{r} < \varepsilon 1 * r + \varepsilon 2;$$

Thus, the threshold th1, th1=ε1*r+ε2, of $$\frac{b}{r}$$

can be obtained. And, the value range of $\varepsilon_1$ is [−1,1], the value range of $\varepsilon_2$ is [−2,5]. Preferably, $\varepsilon_1$=−0.0028, $\varepsilon_2$=1.908.

Therefore, by calculating the blue change value $f_b(i,j)$ of each pixel, and calculating the blue change threshold $T_3$ of each pixel, only the set of pixels when $f_b(i,j) > T_3(i,j)$ is more relevant to blue and the deep stained area S2 can be further calculated. The deep stained area S2 is more accurate compared to the initial range area S, and is more able to reflect the range of blue area in the entire basic image, making the result more accurate.

The present invention further provides a capsule endoscope system. The capsule endoscope system comprises a capsule endoscope and an external device. The external device comprises a memory and a processor. The memory stores computer programs that can run on the processor, and the processor executes the computer programs to implement the steps in the method of identifying stained area in endoscopic images as described above, that is, implement any one of the embodiments in the method of identifying stained area in endoscopic images.

In addition, the present invention further provides a computer readable storage medium for storing computer programs. The computer programs are executed by the processor to implement the steps in the method of identifying stained area in endoscopic images as described above, that is, implement any one of the embodiments in the method of identifying stained area in endoscopic images.

In summary, in the present invention, since the color difference between a lesion site and the normal site on the gastrointestinal mucosa is large after the gastrointestinal tract is stained, it can selectively identify the hue, saturation and value of each pixel and b component of each pixel in the basic image to determine the stained site, and thus to further analyze the recovery of gastrointestinal mucosa and the efficacy of mucosal protective agent. Moreover, in the present invention, abnormal pixels are removed from the basic image to further improve the accuracy of pixel determination.

In addition, the staining condition of the basic image can be determined. If it is identified to be completely stained, the initial range area S1 can be used to calculate the proportion of the stained area; if it is identified that the staining is poor, and the staining is incomplete or inconspicuous, the initial range area S1 cannot be used to calculate the proportion of the stained area, and the calculation of deep stained area S2 is required. The deep stained area S2 provides a basis for identification through the ratio of blue value to other color, even when blue is not clear in the basic image.

Finally, after obtaining the initial range area S1 or the deep stained area S2, the percentage of the stained area can be calculated to determine the healing of mucosa and the effectiveness of mucosal protective agent in the final basic image, which is more scientific and efficient.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The series of detailed descriptions listed above are only specific descriptions of feasible implementations of the present invention, and are not intended to limit the protection scope of the present invention. On the contrary, any equivalent implementations made without departing from the technical spirit of the present invention, the modifications and variations are possible within the scope of the appended claims.

What is claimed is:

1. A method of identifying a stained area in endoscopic images, comprising:
providing a capsule endoscope system comprising a capsule endoscope and an external device,
obtaining a basic image taken by a photographing device within the capsule endoscope, wherein the capsule endoscope is a swallowable device and used in gastrointestinal examinations;

removing abnormal pixels from the basic image and recording the basic image as a processed image after the abnormal pixels are removed;

obtaining a hue, saturation, and value of each pixel in the processed image of HSV format;

setting a first condition for each pixel where the hue is in a D1 range, the saturation is in a D2 range, and the value is in a D3 range;

obtaining a b component of each pixel in the processed image of Lab format;

setting a second condition that the b component of each pixel is in a D4 range;

collecting and processing pixels that meet the first condition and/or the second condition to form a set C;

calculating an initial range area S1 of the set C, wherein the D4 range is [¼Bmin, 0.16], and the b component is normalized, and wherein Bmin is a minimum value of the b component of the basic image in a Lab color model.

2. The method of claim 1, wherein the step of "removing abnormal pixels from the basic image and recording the basic image after as a processed image after the abnormal pixels are removed" comprises:

converting the basic image to a grayscale format;

obtaining a set of pixels with grayscale values in a G range from the basic image and recording the set of pixels with grayscale values in the G range from the basic image as the processed image.

3. The method of claim 2, wherein the G range is [10,240].

4. The method of claim 1, wherein in the step of "setting a first condition for each pixel where the hue is in a D1 range, the saturation is in a D2 range, and the value is in a D3 range", the D1 range is [0.43,0.7], the D2 range is [0.16,1], the D3 range is [0.16,1], and the hue, the saturation, and the value are normalized.

5. The method of identifying the stained area in endoscopic images of claim 1, wherein after the step of "calculating the initial range area S1 of the set C", the method further comprises:

determining staining of the basic image;

when the stained area is completely stained, calculating the ratio of the initial range area S1 of the set C to a total area of the basic image, and obtaining a ratio of the stained area;

when the staining of the stained area is any amount of staining less than a complete staining of the region, calculating a deep stained area S2, calculating a ratio of the deep stained area S2 to the total area of the basic image, and obtaining the ratio of the stained area.

6. The method of claim 5, wherein the step of "determining the staining of the basic image" comprises:

taking 0 as the value of pixels in the processed image with a hue in a range H1, taking 1 as the value of pixels in the processed image with a hue in a range H2, and a minimum value in the range H2 is greater than a maximum value in the range H1;

calculating an area Sh of the pixels whose value is taken as 1;

obtaining a threshold T1;

when Sh>T1, determining that the staining of the stained area in the basic image is poor;

when Sh<T1, determining that the staining of the stained area in the basic image is completely stained.

7. The method of claim 6, wherein the range H1 is [0,$T_2$], the range H2 is [$T_2$, 1], a value range of $T_2$ is [0.01,0.2], a value range of T1 is [0.6,0.98], and the hue of each pixel is normalized.

8. The method of claim 5, wherein the step of "calculating the deep stained area S2" comprises:

calculating a RGB value of each pixel in the processed image, x1(i, j)=(r, g, b);

calculating the HSV value of each pixel in the processed image, x2(i, j)=(h, s, v);

calculating a blue change value fb(i, j) of each pixel, $$fb(i,j)=\alpha*(b/r)+\beta*(b/g)+\gamma(b/h);$$

obtaining a blue change value threshold T3;

obtaining a set of all pixels, of which fb(i, j)>T3, and calculating the deep stained area S2, wherein α, β, γ are used as coefficients to adjust the weight of b/r, b/g, b/h in the blue change value fb(i, j), and wherein a value range of α, β, γ is [0,3].

9. The method of claim 8, wherein the step of "obtaining the blue change value threshold T3" comprises:

calculating the blue change value threshold T3(i, j) of each pixel, $$T3(i,j)=\alpha*th1+\beta*th2+\gamma*th3;$$

th1 is the threshold of b/r, th2 is the threshold of b/g, th3 is the threshold of b/h;

the step "obtaining a set of all pixels, of which fb(i, j)>T3, and calculating the deep stained area S2" comprises:

calculating a magnitude of fb(i, j) and T3(i, j) of each pixel, respectively;

obtaining the set of all pixels, of which fb(i, j)>T3(i, j), and calculating the deep stained area S2, wherein α, β, γ are used as coefficients to adjust the weight of b/r, b/g, b/h in the blue change value fb(i, j), and wherein the value range of α, β, γ is [0,3].

10. The method of claim 9, wherein a relationship between th1 and r of the pixel is obtained by the following formula:

$$th1=\varepsilon_1*r+\varepsilon_2;$$

a value range of $\varepsilon_1$ is [−1,1], a value range of $\varepsilon_2$ is [−2,5].

11. The method of claim 10, wherein a value range of th2 is [0.7,2.2], a value range of th3 is [1,2].

12. A capsule endoscope system, comprising:

a capsule endoscope;

and an external device, comprising a memory and a processor, wherein the memory stores computer programs that run on the processor, and the processor executes the computer programs to implement a method of identifying a stained area in endoscopic images;

wherein the method comprises:

obtaining a basic image taken by a photographing device within the capsule endoscope, wherein the capsule endoscope is a swallowable device and used in gastrointestinal examinations;

removing abnormal pixels from the basic image and recording the basic image as a processed image after the abnormal pixels are removed;

obtaining a hue, saturation, and value of each pixel in the processed image of HSV format;

setting a first condition for each pixel where the hue is in a D1 range, the saturation is in a D2 range, and the value is in a D3 range;

obtaining a b component of each pixel in the processed image of Lab format;

setting a second condition that the b component of each pixel is in a D4 range;

collecting and processing the pixels that meet the first condition and/or the second condition to form a set C;

calculating an initial range area S1 of the set C, wherein the D4 range is [¼Bmin, 0.16], and the b component is normalized, and wherein Bmin is a minimum value of the b component of the basic image in a Lab color model.

13. A computer readable non-transitory storage medium, wherein the computer readable storage medium stores computer programs, and the computer programs are executed by a processor to implement a method of identifying a stained area in endoscopic images, comprising:

obtaining a basic image taken by a photographing device within the capsule endoscope, wherein the capsule endoscope is a swallowable device and used in gastrointestinal examinations;

removing abnormal pixels from the basic image and recording the basic image as a processed image after the abnormal pixels are removed;

obtaining a hue, saturation, and value of each pixel in the processed image of HSV format;

setting a first condition for each pixel where the hue is in a D1 range, the saturation is in a D2 range, and the value is in a D3 range;

obtaining a b component of each pixel in the processed image of Lab format;

setting a second condition that the b component of each pixel is in a D4 range;

collecting and processing pixels that meet the first condition and/or the second condition to form a set C;

calculating an initial range area S1 of the set C, wherein the D4 range is [¼Bmin, 0.16], and the b component is normalized, and wherein Bmin is a minimum value of the b component of the basic image in a Lab color model.

* * * * *